(12) United States Patent
Iwatani et al.

(10) Patent No.: US 7,045,320 B2
(45) Date of Patent: May 16, 2006

(54) METHODS FOR PRODUCING L-AMINO ACIDS

(75) Inventors: Shintaro Iwatani, Kawasaki (JP); Masaki Kobayashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 528 days.

(21) Appl. No.: 10/323,627

(22) Filed: Dec. 20, 2002

(65) Prior Publication Data

US 2003/0138918 A1 Jul. 24, 2003

Related U.S. Application Data

(63) Continuation of application No. 10/050,587, filed on Jan. 18, 2002, now abandoned.

(30) Foreign Application Priority Data

Jan. 19, 2001 (JP) .............................. 2001-011847

(51) Int. Cl.
C12P 13/22 (2006.01)
(52) U.S. Cl. ................. 435/108; 435/106; 435/252.33; 435/252.8
(58) Field of Classification Search ................. 435/108
See application file for complete search history.

(56) References Cited

U.S. PATENT DOCUMENTS

| | | | |
|---|---|---|---|
| 5,763,231 A | 6/1998 | Ono et al. | |
| 5,919,670 A | 7/1999 | Okamoto et al. | |
| 5,932,453 A | 8/1999 | Kikuchi et al. | |
| 6,143,552 A | 11/2000 | Okamoto et al. | |
| 6,319,696 B1 | 11/2001 | Kishino et al. | |
| 6,344,347 B1 | 2/2002 | Kino et al. | |
| 6,361,986 B1 | 3/2002 | Tilg et al. | |

FOREIGN PATENT DOCUMENTS

| | | |
|---|---|---|
| GB | 181 592 | 6/1922 |
| GB | 903 312 | 8/1962 |
| GB | 1 181 592 | 2/1970 |
| WO | 94 08031 | 4/1994 |

OTHER PUBLICATIONS

Aristidou A. et al.,: "Improvement of Biomass Yield and Recombinant Gene Expression In *Escherichia coli* by Using Fructose as the Primary Carbon Source" Biotechnol Prog, vol. 15, No. 1, pp. 140-145 (1999) XP002193799 *the whole document*.

*Primary Examiner*—Herbert J. Lilling
(74) *Attorney, Agent, or Firm*—Cermak & Kenealy, LLP; Shelly Guest Cermak

(57) ABSTRACT

A bacterium belonging to the genus *Escherichia* having an ability to produce an L-amino acid is cultured in a medium containing fructose as a main carbon source, preferably a medium containing a carbon source composed of 30 weight % or more of fructose and 70 weight % or less of glucose, to produce and accumulate the L-amino acid in the medium, and the L-amino acid is collected from the medium.

4 Claims, No Drawings

METHODS FOR PRODUCING L-AMINO ACIDS

FIELD OF THE INVENTION

The present invention relates to methods for producing L-amino acids by fermentation. L-amino acids are widely used as raw materials of drugs, seasonings, feedstuffs and so forth.

DESCRIPTION OF THE RELATED ART

Conventionally, L-amino acids are industrially produced by fermentation using coryneform bacteria that belong to the genus *Brevibacterium* or *Corynebacterium*. In recent years, methods for producing L-amino acids by using bacteria belonging to the genus *Escherichia* such as *Escherichia coli* have also been developed. Moreover, various techniques for increasing L-amino acid producing ability by gene recombination techniques are disclosed (Japanese Patent Laid-open Publication (Kokai) No. 57-71397; U.S. Pat. No. 4,371,614).

It has been reported that, if fructose is used as a carbon source during mass production of proteins, production of acetic acid is reduced and the microbial cell yield increases (*Biotechnol. Prog.*, 15, pp.140–145, 1999). However, the relationship between fructose and L-amino acid production remains unknown.

DISCLOSURE OF THE INVENTION

As described above, productivity of L-amino acids has been considerably increased by breeding of microorganisms and improvement of production methods. However, in order to respond to further increase in their demands in future, development of further inexpensive and efficient methods for producing L-amino acids are being desired.

An object of the present invention is to provide a technique for improving the L-amino acid productivity of bacteria belonging to the genus *Escherichia*.

The inventors of the present invention assiduously studies in order to achieve the aforementioned object. As a result, they found that, if fructose was used as a carbon source of a medium used for culture of a bacterium belonging to the genus *Escherichia*, L-amino acid producing ability was improved, and accomplished the present invention.

That is, the present invention provides the followings.

(1) A method for producing an L-amino acid, which comprises culturing a bacterium belonging to the genus *Escherichia* having an ability to produce the L-amino acid in a medium containing fructose as a main carbon source to produce and accumulate the L-amino acid in the medium and collecting the L-amino acid from the medium.

(2) The method for producing an L-amino acid according to (1), wherein the medium contains 30 weight % or more of fructose with respect to the total amount of carbon source.

(3) The method for producing an L-amino acid according to (1), wherein the medium contains 30 weight % or more but 95 weight % or less of fructose with respect to the total amount of carbon source.

(4) The method for producing an L-amino acid according to (1), wherein the medium contains 30 weight % or more of fructose and 70 weight % or less of glucose with respect to the total amount of carbon source.

(5) The method for producing an L-amino acid according to any one of (1) to (4), wherein the bacterium belonging to the genus *Escherichia* is *Escherichia coli*.

(6) The method for producing an L-amino acid according to any one of (1) to (5), wherein the L-amino acid is L-tryptophan.

In the present specification, "L-amino acid producing ability" or "ability to produce an L-amino acid" refers to an ability to accumulate a significant amount of an L-amino acid in a medium or to increase L-amino acid content in microbial cells when a bacterium belonging to the genus *Escherichia* is cultured in the medium.

In the present invention, as the L-amino acid, there can be mentioned L-tryptophan, L-phenylalanine, L-lysine, L-threonine, L-valine, L-leucine, L-isoleucine, L-homoserine, L-glutamic acid and so forth.

Bacteria used in the present invention are not particularly limited so long as they are bacteria belonging to the genus *Escherichia* and have L-amino acid producing ability. Specific examples of the bacteria belonging to the genus *Escherichia* include those mentioned in the work of Neidhardt et al. (Neidhardt, F. C. et al., *Escherichia coli* and *Salmonella Typhimurium*, American Society for Microbiology, Washington D.C., 1208, Table 1) and derivatives derived from these bacteria.

*Escherichia coli* having L-amino acid producing ability may be a mutant or recombinant strain. As the mutant, there can be mentioned mutants having a mutation that increases an activity of intracellular enzyme involved in biosynthesis of an L-amino acid, specifically, a mutation that increases an expression amount of the enzyme or a mutation that eliminates feedback inhibition. Further, as the recombinant strain, there can be mentioned a strain having an increased copy number of a gene coding for an enzyme involved in L-amino acid biosynthesis, a strain of which expression control sequence is modified to increase expression amount of the gene, a strain introduced with a gene coding for an enzyme of which feedback inhibition is eliminated and so forth.

The mutants can be obtained by treating wild strains of bacteria belinging to the genus *Escherichia* or derivatives thereof by UV irradiation or with mutagenizing agents used for a usual mutagenesis treatment such as N-methyl-N'-nitro-N-nitrosoguanidine (NTG) and nitrous acid.

In order to increase copy number of a gene, the target gene and a vector functioning in a bacterium belonging to the genus *Escherichia* may be ligated to prepare recombinant DNA, and the bacterium belonging to the genus *Escherichia* may be transformed with the recombinant DNA. Further, the transformation can be performed by the method of D. A. Morrison (*Methods in Enzymology*, 68, p.326, 1979), the method of treating recipient cells with calcium chloride so as to increase the permeability of DNA (Mandel, M. and Higa, A., *J. Mol. Biol.*, 53, p.159, 1970) and so forth. As the aforementioned vector, there can be mentioned pUC19, pUC18, pUC118, pUC119, pBR322, pHSG299, pHSG298, pHSG399, pHSG398, RSF1010, pMW119, pMW118, pMW219, pMW218, pSTV28, pSTV29 and so forth, and additionally, phage vectors can also be used.

The copy number of a gene can be increased also by presence of multiple copies of the target gene on chromosomal DNA of a bacterium belonging to the genus *Escherichia*. In order to introduce multiple copies of the target gene into chromosomal DNA of the bacterium belonging to the genus *Escherichia*, homologous recombination is performed by using, as a target, a sequence that is present on the chromosomal DNA in a multiple copy number. As a sequence present on chromosomal DNA in a multiple copy number, repetitive DNA or inverted repeats present at the ends of transposable elements can be used. Alternatively, as disclosed in Japanese Patent Laid-open Publication (Kokai) No. 2-109985, multiple copies of the target gene can be introduced into chromosomal DNA by mounting each of them on a transposon to transfer them.

Activity of a target enzyme can be increased by replacing an expression control sequence such as a promoter of a gene coding for the target enzyme with a stronger one (Japanese Patent Laid-open Publication (Kokai) No. 1-215280). As such strong promoters, there have been known, for example, lac promoter, trp promoter, trc promoter, tac promoter, $P_R$ promoter and $P_L$ promoter of lamda phage, tet promoter, amyE promoter and so forth.

Hereafter, a method for breeding L-tryptophan producing bacteria as L-amino acid producing bacteria belonging to the genus *Escherichia* and their specific bacterial strains will be exemplified.

Examples of enzymes involved in L-tryptophan biosynthesis include 3-deoxy-D-arabino-heptulonate-7-phosphate synthase of the L-tryptophan biosynthesis system (Japanese Patent Laid-open Publication (Kokai) No. 5-236947), transketolase (U.S. Pat. No. 5,906,925), anthranilate synthase (WO94/08031 (International Patent Unexamined Publication in Japanese (Kohyo) No. 7-507693)), phosphoglycerate dehydrogenase (WO94/08031) and so forth. Among these enzymes, anthranilate synthase is known to suffer feedback inhibition by L-tryptophan, and phosphoglycerate dehydrogenase is known to suffer feedback inhibition by L-serine.

As L-tryptophan producing bacteria belonging to the genus *Escherichia* used in the present invention, preferred are bacteria belonging to the genus *Escherichia* harboring desensitized anthranilate synthase, desensitized phosphoglycerate dehydrogenase, or both of them. A bacterium belonging to the genus *Escherichia* having such a property can be obtained by, for example, mutating the anthranilate synthase gene (trpE) and/or the phosphoglycerate dehydrogenase gene (serA) so as not to suffer feedback inhibition and introducing the obtained mutant gene into the bacterium belonging to the genus *Escherichia*. More specifically, as such a bacterium belonging to the genus Escherichia, there can be mentioned a transformant strain obtained by introducing a plasmid pGH5 (WO94/08031) containing a mutant serA coding for desensitized phosphoglycerate dehydrogenase into *Escherichia coli* SV164 containing desensitized anthranilate synthase.

Further, a bacterium belonging to the genus *Escherichia* introduced with recombinant DNA containing a tryptophan operon is also a preferred L-tryptophan producing bacterium. Specifically, there can be mentioned *Escherichia coli* introduced with a tryptophan operon containing a gene coding for desensitized anthranilate synthase (Japanese Patent Laid-open Publication (Kokai) Nos. 57-71397 and 62-244382; U.S. Pat. No. 4,371,614).

Further, as L-tryptophan producing bacteria, there can be mentioned *Escherichia coli* AGX17(pGX44) [NRRL B-12263], which is a bacterial strain having a phenotype of L-phenylalanine and L-tyrosine auxotrophy, and the AGX6 (pGX50)aroP [NRRL B-12264] strain, which harbors a plasmid pGX50 containing a tryptophan operon (refer to U.S. Pat. No. 4,371,614 for the both).

Further, the L-tryptophan producing ability can be enhanced by increasing the phosphoenolpyruvate producing ability in a cell of a bacterium belonging to the genus *Escherichia* having L-tryptophan producing ability (WO97/08333).

The aforementioned genes or operons of enzymes can be obtained by a usual gene isolation method well known to those skilled in the art. For example, a target gene can be obtained by synthesizing primers based on a known sequence, and performing PCR by using chromosomal DNA of a bacterium belonging to the genus *Escherichia* such as the *Escherichia coli* K-12 strain as a template.

As methods for gene cloning and introducing DNA into a host including preparation of chromosomal DNA, preparation of a chromosomal DNA library, hybridization, PCR, preparation of plasmid DNA, digestion and ligation of DNA, transformation, design of oligonucleotides used as primers and so forth, usual methods well known to those skilled in the art can be used. Such methods are described in Sambrook, J., Fritsch, E. F., and Maniatis, T., "Molecular Cloning, A Laboratory Manual, 2nd Edition", Cold Spring Harbor Laboratory Press, 1989 and so forth.

Hereafter, other L-amino acid producing bacteria will be exemplified.

As an L-phenylalanine producing bacterium, there can be mentioned *Escherichia coli* AJ12604 (FERM BP-3579) (European Patent Laid-open Publication No. 488,424).

As an L-lysine producing bacterium belonging to the genus *Escherichia*, there can be exemplified a mutant having resistance to an L-lysine analogue. The L-lysine analogue is such one which inhibits growth of bacteria belonging to the genus *Escherichia*, but the inhibition is fully or partially eliminated when L-lysine coexists in a medium. Examples thereof include oxalysine, lysine hydroxamate, (S)-2-aminoethyl-L-cysteine (AEC), γ-methyllysine, α-chlorocaprolactam and so forth. Mutants having resistance to these lysine analogues can be obtained by subjecting a microorganism belonging to the genus *Escherichia* to a usual artificial mutation treatment. Specific examples of bacterial strains used for production of L-lysine include *Escherichia coli* AJ11442 (FERM BP-1543, NRRL B-12185; refer to Japanese Patent Laid-open (Kokai) No. 56-18596 and U.S. Pat. No. 4,346,170) and *Escherichia coli* VL611. The AJ11442 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, 1–3 Higashi 1-chome, Tsukuba-shi, Ibaraki-ken, 305-8566, Japan) on May 1, 1981 and received an accession number of FERM P-5084. Then, it was transferred to an international deposit under the provisions of the Budapest Treaty on Oct. 29, 1987 from the above original deposit, and received an accession number of FERM BP-1543. The feedback inhibition of aspartokinase by L-lysine is desensitized in the above microorganisms.

In addition, there can also be mentioned L-threonine producing bacteria. This is because, in L-threonine producing bacteria, inhibition of aspartokinase by L-lysine is generally eliminated. As L-threonine producing bacteria of *Escherichia coli*, there can be mentioned *Escherichia coli* MG442 (refer to Gusyatiner et al., *Genetika* (in Russian), 14, pp.947–956, 1978).

A gene encodes an L-lysine biosynthesis enzyme may be enhanced in the aforementioned L-lysine producing bacterium. Examples of such a gene include a gene coding for phosphoenolpyruvate carboxylase having a mutation for desensitizing feedback inhibition by aspartic acid (Japanese Patent Publication (Kokoku) No. 7-83714).

As a specific example of L-valine producing bacteria belonging to the genus Escherichia, there can be mentioned *Escherichia coli* VL1970 (VKPM B-4411) (European Patent Publication No. 519,113).

Other than the above, there can be mentioned bacteria belonging to the genus *Escherichia* containing L-valine biosynthesis gene of which control mechanism is substantially eliminated. Such bacteria belonging to the genus *Escherichia* can be obtained by, for example, introducing an ilvGMEDA operon, preferably, an ilvGMEDA operon which does not express threonine deaminase activity and in which attenuation is eliminated, into a bacterium belonging to the genus *Escherichia* (refer to Japanese Patent Laid-open Publication (Kokai) No. 8-47397).

Since the whole nucleotide sequence of the ilvGMEDA operon has been revealed (*Nucleic Acids Res.*, 5, p.2137, 1987), it can be obtained from chromosomal DNA of *Escherichia coli* by colony hybridization or PCR using oligonucleotides prepared based on the sequence. A DNA fragment containing the ilvGMEDA operon can be introduced into *Escherichia coli* by the aforementioned method using a plasmid, phage or transposon.

Examples of L-leucine producing bacteria belonging to the genus *Escherichia* include a strain having β-2-thienylalanine resistance, a strain having β-2-thienylalanine resistance and β-hydroxyleucine resistance (Japanese Patent Publication (Kokoku) No. 62-34397 for the above) and a strain having 4-azaleucine resistance or 5,5,5-trifluoroleucine resistance (Japanese Patent Laid-open Publication (Kokai) No. 8-70879).

As L-isoleucine producing bacteria belonging to the genus *Escherichia*,there can be mentioned *Escherichia coli* KX141 (VKPM B-4781) (European Patent Publication No. 519,113).

As L-threonine producing bacteria belonging to the genus *Escherichia*,there can be mentioned *Escherichia coli* VKPM B-3996 (RIA 1867) (U.S. Pat. No. 5,175,107) and the MG442 strain.

As L-homoserine producing bacteria belonging to the genus *Escherichia*,there can be mentioned the NZ10 strain, which is a Leu$^+$ revertant of the C600 strain (Appleyard R. K., *Genetics*, 39, pp.440–452, 1954).

As L-glutamic acid producing bacteria belonging to the genus *Escherichia*,there can be mentioned L-valine resistant strains such as *Escherichia coli* B11, *Escherichia coli* K-12 (ATCC 10798), *Escherichia coli* B (ATCC 11303) and *Escherichia coli* W (ATCC 9637).

In the present invention, a medium containing fructose as a main carbon source is used when a bacterium belonging to the genus *Escherichia* having L-amino acid producing ability is cultured. The yield with respect to sugar and the production rate of L-amino acids are improved by using fructose as a main carbon source.

The carbon source may substantially consist only of fructose or may also contain carbon sources other than fructose. The fructose content is preferably 30 weight % or more, preferably about 30–95 weight %, more preferably about 30–70 weight %, particularly preferably about 50%, with respect to the total carbon source. Other carbon sources include glucose, sucrose, maltose and so forth. Among these, glucose is preferred. A specific example of the carbon source used in the present invention is a mixture of 30 weight % or more of fructose and 70 weight % or less of glucose.

Medium components other than the carbon source are usual medium components such as nitrogen source, inorganic ions and organic trace nutrients used as required.

As the nitrogen source, there can be used inorganic ammonium salts such as ammonium sulfate, ammonium chloride and ammonium phosphate, organic nitrogen such as soybean hydrolysate, ammonia gas, aqueous ammonia and so forth.

As the inorganic ions or source thereof, small amounts of potassium phosphate, magnesium sulfate, iron ion, manganese ion and so forth are added. As the organic trace nutrients, required substances such as vitamin $B_1$, yeast extract and so forth are desirably contained in appropriate amounts as required.

The culture may be performed under a condition selected depending on the used bacterial strain, but, specifically, it is preferably performed under an aerobic condition for 16–72 hours. The culture temperature is regulated to be 30–45° C. and pH is regulated to be 5–7 during the culture. An inorganic or organic, acidic or alkaline substance and further an ammonia gas or the like can be used for pH adjustment.

Collection of L-amino acids from fermented liquor can be attained by appropriately combining known methods such as those utilizing ion exchange resin, precipitation and others.

According to the present invention, the yield with respect to sugar and/or the production rate can be improved in methods for producing L-amino acids such as L-tryptophan by using bacteria belonging to the genus *Escherichia*.

BEST MODE FOR CARRYING OUT THE INVENTION

Hereafter, the present invention will be explained more specifically with reference to the following examples.

<1> Construction of L-Tryptophan Producing Strain of *Escherichia Coli*

According to the description in WO94/08031 (International Patent Unexamined Publication in Japanese (Kohyo) No. 7-507693), a trpE deficient strain, *Escherichia coli* KB862 (DSM7196), was introduced with a mutant gene coding for anthranilate synthase of which feedback inhibition was desensitized (also referred to as "desensitized AS" hereafter) to obtain *Escherichia coli* SV164 (trpE8). This SV164 strain was introduced with a plasmid pGH5 (described in WO94/08031) containing a gene coding for phosphoglycerate dehydrogenase of which feedback inhibition was desensitized (also referred to as "desensitized PGD" hereafter). The SV164/pGH5 strain had ability to produce tryptophan and serine.

*Escherichia coli* KB862 was designated as AJ13828, and deposited at the National Institute of Bioscience and Human-Technology, Agency of Industrial Science and Technology (currently, National Institute of Advanced Industrial Science and Technology, International Patent Organism Depositary, 1–3 Higashi 1-chome, Tsukuba-shi, Ibaraki-ken, 305–8566, Japan) as an international deposit on Dec. 21, 2000 under the provisions of the Budapest Treaty and received an accession number of FERM BP-7405.

Construction method of SV164/pGH5 will be explained below.

(1) Screening of Mutant Gene Coding for Desensitized AS and Incorporation of This Mutant Gene into Chromosome A mutant strain containing inhibition desensitized AS was screened by using 5-methyltryptophan, which is a tryptophan analogue.

*E. coli* K12 YMC9 (ATCC 33927) was subjected to a mutagenesis treatment with N-methyl-N'-nitro-N-nitrosoguanidine (NG) according to the method of Miller (Miller J. H., Experiments in Molecular Genetics, Cold Spring Harbor Laboratory, Cold Spring Harbor, N.Y., pp.125–129, 1972). That is, about $2 \times 10^9$ of YMC9 cells were incubated in 4 ml of 0.1 M sodium citrate buffer (pH 5.5) containing 50 μg/ml of NG at 37° C. for 30 minutes. The cells were washed twice with 0.1 M sodium phosphate buffer (pH 7.0), and the cells in an amount of 0.1 ml were cultured overnight at 37° C. in LB medium with shaking. Subsequently, the culture broth was diluted with 0.9% NaCl to dilutions of $10^{-3}$, $10^{-4}$ and $10^{-5}$, and 0.1 ml of each diluted solution was applied on a minimal medium plate containing 100 μg/ml of 5-methyltryptophan. The composition of the minimal medium included 5 g/l of glucose, 5 mg/l of vitamin $B_1$, 3 g/l of $KH_2PO_4$, 12 g/l of $K_2HPO_4$, 0.3 g/l of $MgSO_4.7H_2O$, 0.1 g/l of NaCl, 5 g/l of $(NH_4)_2SO_4$, 14.7 mg/l of $CaCl_2.2H_2O$, 2 mg/l of $FeSO_4.7H_2O$, 1 g/l of trisodium citrate and 15 g/l of agar.

Following the culture for 24–48 hours at 37° C., 5-methyltryptophan resistant clones were seeded on the aforementioned agar medium. In order to examine properties of the obtained mutant strain, Ki value of AS to L-tryptophan was measured (Bauerle R. et al., *Methods in Enzymology*, 142, pp.366–386, 1987). As a result, the mutant strains could be classified into two classes. The class 1 mutant strains had feedback resistant anthranilate synthase. The class 2 mutant strains had a high anthranilate synthase activity although their Ki value was unaltered. The AS genes of these mutant strains were cloned and their nucleotide sequences were determined. Chromosomal DNA of each mutant strain was isolated and digested with restriction enzymes NheI and ClaI to isolate a fragment of about 5 kb, and this fragment was ligated with the NheI/ClaI fragment (4158 bp) of pBR322.

*E. coli* KB 862 (trpE) (DSM7196) was transformed with the ligation reaction product. A clone that could grow on a minimal medium not containing L-tryptophan was selected. All the plasmids complementing the trpE mutation contained the NheI/ClaI fragment of 5 kb. Further, this 5 kb NheI/ClaI fragment contained trpE, trpD, a sequence about 0.8 kb upstream from trpE, and a sequence about 1 kb downstream from trpD. Differences in amino acid sequences of mutant AS encoded by plasmids (pE0, pE5, pE6, pE8) contained in the mutant strains and their Ki values are shown in Table 1.

TABLE 1

| Enzyme | Amino acid sequence | Ki/mM |
|---|---|---|
| Wild type trpE | NPTA LFHQ LCGD RPAT LLLE SADI DSKD DLKS (SEQ ID NO: 1) | 0.01 |
| TrpE0 | ------------------------------------E- | 0.1 |
| TrpE5 | -S------------------------------------ | 3.0 |
| TrpE6 | ------------------------F----------E- | >15 |
| TprE8 | -S------------------------------------E- | 15 |

Sequence analysis of the class 2 mutant enzymes demonstrated that the mutation existed both in the operator region of the trp promoter and a DNA region coding for the trp leader peptide. The mutations designated as ΔtrpL1 and ΔtrpL2 had deletion in a size of 136 bp or 110 bp in the DNA region coding for the leader peptide. In the sequence registered at the EMBL Data Bank as an accession No. V00372, deletion of the region of the 33–168th positions was included in the ΔtrpL1 mutation, while deletion of the region of the 11-120th positions was included in the ΔtrpL2 mutation.

The two mutant classes were combined to highly express the gene coding for the desensitized AS. For the class 2 strain, the ΔtrpL1 mutation was used. A 1.6 kb NruI fragment having the ΔtrpL1 mutation was isolated from the plasmid pΔtrpL and replaced with a corresponding NruI fragment in the plasmid pE0, pE5, pE6 or pE8. The obtained plasmids were designated as pIE0, pIE5, pIE6 and pIE8 and used for incorporation into chromosome by homologous recombination.

About 5 kb NheI/ClaI fragment was isolated from each plasmid by using a low melting point agarose, and used in a linear state to transform a recD strain, PD106 [ΔtrpLD102]. As the transformation method, the $CaCl_2$ method according to Cohen et al., *Proc. Natl. Acad. Sci. USA*, 69, 2, pp.110–2114, 1972 was used. A clone that could grow on a minimal medium not containing L-tryptophan and was ampicillin susceptible, that is, did not contain the plasmid, was selected. The mutant trpE gene coding for the desensitized AS and having the ΔtrpL1 mutation was transferred from each bacterial strain to the KB862 strain by P1 transduction (Miller J. H., Experiments in Molecular Genetics, Cold Spring Harbor, N.Y., pp.201–205, 1972) and selected in a minimal medium not containing tryptophan. The obtained bacterial strains were designated as PD103 (trpE0), KB862 (trpE5), SV164 (trpE8) and SV163 (trpE6).

(2) Preparation of serA Gene Encoding Desensitized PGD

A serA gene coding for PGD was cloned from the *E. coli* B strain (ATCC 23226) into the plasmid vector pUC18. The B strain was cultured overnight at 37° C. in LB. The cells were collected by centrifugation (4000×g), and chromosomal DNA was prepared by the method described in Ausubel et al., Current Protocols in Molecular Biology, Greene Publishing Associates 2.4.1–2.4.2, 1987. In an amount of 10 μg of chromosomal DNA was digested with SphI. About 3 μg of the digested product was ligated with 0.2 μg of plasmid pUC18 similarly digested with SphI. The serA mutant PC1523 (CGSC No. 5411) (CGSC: *E. coli* Genetic Stock Center, Department of Biology 255 OML, Yale University, Postbox 6666, New Haven, Conn., USA) was transformed with the ligation reaction mixture by the aforementioned method of Cohen et al.

The transformant strains were applied on a minimal medium not containing L-serine. The grown clones contained the *E. coli* serA gene in a 3.5 kb SphI fragment. The sequence of the wild type serA gene is described in WO94/08031. The recombinant vector having the serA gene was designated as pGC3.

By using the wild type serA gene obtained as described above, a serA gene coding for desensitized PGD of which C-terminus amino acid was deleted was prepared. pGC3 was digested with SalI and KpnI, and the obtained fragment was separated by agarose gel electrophoresis. A 2.0 kb SalI-KpnI fragment including the full length of the serA gene was purified from the gel. In an amount of 0.2 μg of this fragment and equimolar amounts of HindIII/SalI-digested pUC18 and a double-stranded oligonucleotide obtained by annealing oligonucleotides having the nucleotide sequences of SEQ ID NOS: 2 and 3 were ligated. This oligonucleotide complemented 7 of the last 8 C-terminus codons of the serA gene and introduced a termination codon TAA instead of the 8th codon. Therefore, PGD encoded by this mutant serA gene was shortened by one amino acid residue of the C-terminus. The plasmid containing this mutant serA gene was designated as pGH5. The desensitized PGD encoded by the gene had a Ki value of 0.1–50 μM to serine, and its feedback inhibition by serine was desensitized.

<2> Production of L-Tryptophan

The aforementioned tryptophan producing bacterium, *Escherichia coli* SV164/pGH5, was inoculated into 50 ml of LB medium (1% trypton, 0.5% yeast extract, 0.5% sodium chloride) in a 500-ml volume conical flask and precultured with shaking (150 rpm) at 30° C. for 7–8 hours.

About 1 ml of the aforementioned preculture was inoculated into 300 ml of seed culture medium having the composition shown below. The culture was performed at 30° C. for 11–15 hours at 800 rpm by using a 1-L volume small-size fermenter.

[Seed Culture Medium Composition]

| | |
|---|---|
| Glucose | 5 g/L |
| $KH_2PO_4$ | 12 g/L |
| $(NH_4)_2SO_4$ | 0.1 g/L |
| $MgSO_4.7H_2O$ | 0.3 g/L |
| $CaCl_2.2H_2O$ | 15 mg/L |
| $FeSO_4.7H_2O$ | 2 mg/L |
| $Na_2$ Citrate.$2H_2O$ | 1 g/L |
| Trace element solution | 1 mg/L |
| L-Phenylalanine | 40 mg/L |
| L-Tyrosine | 40 mg/L |
| Vitamin $B_1$ | 5 mg/L |
| Tetracycline | 15 mg/L |
| (Trace element solution) | |
| $Na_3MoO_4$ | 0.15 g/L |
| $H_3BO_3$ | 2.5 g/L |
| $CoCl_2.6H_2O$ | 0.7 g/L |
| $CuSO_4.5H_2O$ | 0.25 g/L |
| $MnCl_2.4H_2O$ | 1.5 g/L |
| $ZnSO_4.7H_2O$ | 0.3 g/L |

In an amount of 30 ml of the above seed culture broth was inoculated into 300 ml of a main culture medium having the composition shown below. By using a 1-L volume small-size fermenter, the medium was cultured at 30° C. with stirring at 800 rpm and aeration at 1 vvm of compressed air sterilized by a sterilization filter. Further, during the culture period, the temperature was maintained at 31° C., and pH was maintained at 6.7 with an ammonia gas.

[Main culture medium composition]

| | |
|---|---|
| Glucose | 17.5 g/L |
| $KH_2PO_4$ | 1.5 g/L |
| $(NH_4)_2SO_4$ | 5 g/L |
| NaCl | 0.5 g/L |
| $MgSO_4.7H_2O$ | 0.3 g/L |
| $CaCl_2.2H_2O$ | 15 mg/L |
| $FeSO_4.7H_2O$ | 75 mg/L |
| $Na_2$ Citrate.$2H_2O$ | 1 g/L |
| Trace element solution | 1 mg/L |
| L-Phenylalanine | 750 mg/L |
| L-Tyrosine | 750 mg/L |
| Vitamin $B_1$ | 5 mg/L |
| Yeast extract | 2.5 g/L |
| Trytone | 2.5 g/L |
| Tetracycline | 20 mg/L |
| (Trace element solution) | |
| $Na_3MoO_4$ | 0.15 g/L |
| $H_3BO_3$ | 2.5 g/L |
| $CoCl_2.6H_2O$ | 0.7 g/L |
| $CuSO_4.5H_2O$ | 0.25 g/L |
| $MnCl_2.4H_2O$ | 1.5 g/L |
| $ZnSO_4.7H_2O$ | 0.3 g/L |

During the culture, the sugar concentration in the small-size fermenter was adjusted to 5–20 g/L by pumping 700 g/L (W/V) of sugar solution having one of the compositions shown in Table 2 (sterilized by autoclaving). After 48 hours of culture, the L-tryptophan concentration in the medium was measured. The yield with respect to sugar and the production rate are shown in Table 3. Table 3 shows ratios when the value of G100 is taken as 1.

TABLE 2

Composition of carbon source

| | G100 | G30F70 | G50F50 | G70F30 | F100 |
|---|---|---|---|---|---|
| Glucose (%) | 100 | 30 | 50 | 70 | 0 |
| Fructose (%) | 0 | 70 | 50 | 30 | 100 |

TABLE 3

Production yield and production rate of L-tryptophan

| | G100 | G30F70 | G50F50 | G70F30 | F100 |
|---|---|---|---|---|---|
| Yield | 1 | 1.14 | 1.27 | 1.19 | 1.22 |
| Production rate | 1 | 1.41 | 1.47 | 1.42 | 1.34 |

Ratio when the value of G100 is taken as 1

As a result, it was found that, when glucose is mixed with fructose, both of the yield with respect to sugar and the production rate were improved compared with the case where a 100% glucose sugar solution was flown down. In particular, when the proportion of fructose to the carbon source was around 50%, the highest productivity was observed.

What is claimed is:

1. A method for producing an L-amino acid comprising:
    a) culturing in a medium an *Escherichia* bacterium which has an ability to produce the L-amino acid, and
    b) collecting the L-amino acid from the medium, wherein said medium contains 30% by weight or more of fructose with respect to the total amount of carbon source present in the medium, wherein the L-amino acid comprises L-tryptophan.

2. The method for producing an L-amino acid according to claim 1, wherein the medium contains 30–95% by weight of fructose with respect to the total amount of carbon source present in the medium.

3. The method for producing an L-amino acid according to claim 1, wherein the medium contains 30% by weight or more of fructose, and 70% by weight or less of glucose, with respect to the total amount of carbon source present in the medium.

4. The method for producing an L-amino acid according to claim 1, wherein the *Escherichia* bacterium comprises *Escherichia coli*.

* * * * *

SEQUENCE LISTING

<160> NUMBER OF SEQ ID NOS: 3

<210> SEQ ID NO 1
<211> LENGTH: 32
<212> TYPE: PRT
<213> ORGANISM: Escherichia coli

<400> SEQUENCE: 1

```
Asn Pro Thr Ala Leu Phe His Gln Leu Cys Gly Asp Arg Pro Ala Thr
1               5                   10                  15

Leu Leu Leu Glu Ser Ala Asp Ile Asp Ser Lys Asp Leu Lys Ser
            20              25              30

<210> SEQ ID NO 2
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
cattcgcgcc cgtctgctgt aata                                          24

<210> SEQ ID NO 3
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ctaggtaagc gcgggcagac gacattattc ga                                 32
```